United States Patent

Henderson

[11] Patent Number: 5,801,055
[45] Date of Patent: Sep. 1, 1998

[54] MULTI-WELL CULTURE DISH ASSEMBLY

[75] Inventor: Douglas P. Henderson, Morristown, N.J.

[73] Assignee: Becton Dickinson and Company, Franklin Lakes, N.J.

[21] Appl. No.: 926,562

[22] Filed: Sep. 10, 1997

[51] Int. Cl.⁶ .................................................. C12M 3/00
[52] U.S. Cl. ................... 435/297.5; 435/305.2; 435/305.3; 422/101; 422/102
[58] Field of Search .............. 435/297.5, 305.1, 435/305.2, 305.3, 305.4; 422/101, 102

[56] References Cited

U.S. PATENT DOCUMENTS

| | | | |
|---|---|---|---|
| 4,407,943 | 10/1983 | Cole et al. | 435/7 |
| 4,871,674 | 10/1989 | Matsui et al. | 435/284 |
| 5,026,649 | 6/1991 | Lyman et al. | 435/284 |
| 5,366,893 | 11/1994 | Stevens et al. | 435/284 |
| 5,462,874 | 10/1995 | Wolf et al. | 435/297.5 |
| 5,487,872 | 1/1996 | Hafeman et al. | 422/102 |
| 5,534,227 | 7/1996 | Lahm et al. | 422/102 |
| 5,554,536 | 9/1996 | Rising | 435/305.1 |

*Primary Examiner*—David A. Redding
*Attorney, Agent, or Firm*—Bruce S. Weintraub

[57] ABSTRACT

A multi-well culture dish assembly is provided which includes an insert having rows of frustoconical enclosures and a well plate in which the enclosures are suspended. The insert includes a top wall having a peripheral flange, the enclosures being integral with and extending downwardly from the top wall. Each enclosure includes a radial opening which extends into the upper portion of the enclosure. Rows of openings are formed in the top wall of the insert, and respectively adjoin the radial openings in the enclosures. The relatively large pipette openings are formed by the adjoining openings. The well plate may include rows of cylindrical wells. The enclosures are positioned within the wells and are radially offset with respect thereto. The openings within the top wall of the insert are in registration with the wells when the insert is mounted to the well plate.

20 Claims, 9 Drawing Sheets

MULTI-WELL CULTURE DISH ASSEMBLY

BACKGROUND OF THE INVENTION

1. Field of the Invention

The invention relates to an apparatus which is useful for growing and/or testing biological materials through the use of inserts including microporous membranes and wells in which such inserts are suspended.

2. Description of the Related Art

Assemblies of various types have been developed which include inserts having microporous membranes and wells in which the membranes are suspended. Such assemblies have been used for culturing cells and/or testing other biological materials. The compositions of the microporous membranes are selected in accordance with the intended use of assemblies of this type.

The inserts of such assemblies may be constructed individually, defining a single enclosure having a substantially impermeable side wall and a semi-permeable bottom wall. U.S. Pat. Nos. 4,686,190, 4,871,674, 5,026,649, 5,366,893 and 5,534,227 disclose inserts meeting this description. Other inserts include a plurality of enclosures joined at or near their openings by a connecting wall. U.S. Pat. Nos. 4,407,943, 5,462,874 and 5,554,536 disclose examples of this type of insert, as does International Publication No. WO 94/28111. U.S. Pat. No. 5,487,872 discloses a well plate comprising rows of cylindrical wells.

The need to add fluid to or remove fluid from the wells in which the above-described inserts are positioned has long been recognized. Many of the above-identified patents accordingly disclose features for allowing pipette access to the wells without displacing the inserts.

SUMMARY OF THE INVENTION

The invention is directed to a culture dish assembly and an insert for use in such an assembly. The assembly includes features which facilitate pipette access to selected portions thereof, minimize the possibility of contamination, and allow the use of robotics in handling assembly components.

A culture dish assembly according to the invention includes a well plate and an insert. The well plate defines one or more wells. The insert includes a top wall and a plurality of enclosures coupled to the top wall. Each enclosure includes an upper end defining an upper opening, a lower end defining a bottom opening, a side wall connecting the upper and lower ends, and a semipermeable membrane mounted to the lower end and covering the bottom opening. A plurality of wall openings are provided in the top wall. Each wall opening adjoins one of the enclosures. Each enclosure includes a radial opening extending through the side wall and upper end thereof and adjoining one of the wall openings. The portions of the side walls adjoining the radial openings are substantially vertical with respect to the top wall of the insert. The adjoining openings and the vertical side portions of the enclosures create a relatively large space capable of receiving a pipette. The end of the pipette preferably avoids engaging any portion of the wells or enclosures when inserted through the adjoining openings.

An insert for a culture dish assembly is also provided by the invention. The insert includes a top wall having at least one row of wall openings. A plurality of enclosures are coupled to the top wall and respectively adjoin the wall openings. Each of the enclosures includes an upper end defining an upper opening, a lower end defining a bottom opening, and a side wall connecting the upper and lower ends. A radial opening extends through each side wall and a portion of the upper end of each enclosure. The radial openings adjoin the respective wall openings, thereby defining relatively large pipette openings. Each of the enclosure side walls includes a substantially vertical portion adjoining the radial opening and extending towards the lower end thereof Each of the enclosure side walls is preferably generally frustoconical, and the substantially vertical portions thereof preferably include substantially flat exterior surfaces.

A culture dish assembly which includes a well plate, insert and lid is provided. The well plate of the assembly includes a plurality of wells, which are preferably cylindrical. The insert includes a top wall, a peripheral flange extending downwardly from the top wall, and a plurality of enclosures coupled to the top wall. Each of the enclosures includes an upper end defining an upper opening, a lower end defining a bottom opening, a side wall connecting the upper and lower ends, a semipermeable membrane mounted to the lower end and covering the bottom opening, and a radial opening extending through the side wall and upper end. The radial openings adjoin openings extending through the top wall of the insert, defining relatively large pipette openings. Each of the side walls includes a substantially vertical portion adjoining the radial opening therein and extending towards the lower end thereof The insert is mountable to the well plate such that the enclosure are positioned within the wells, and preferably in radially offset positions therein. The lid includes a top wall and a downwardly depending peripheral flange. It is mountable to the insert such that the top wall of the lid engages the upper ends of the enclosures. The peripheral flange of the lid overlies the upper portion of the peripheral flange of the insert when the lid is applied to the insert. The lower portion of the peripheral flange of the insert remains exposed and therefore accessible beneath the peripheral flange of the lid. The insert and lid may accordingly be handled as a unit, thereby minimizing the possibility of contaminating the contents of the enclosures.

DETAILED DESCRIPTION OF THE INVENTION

Figure 1:
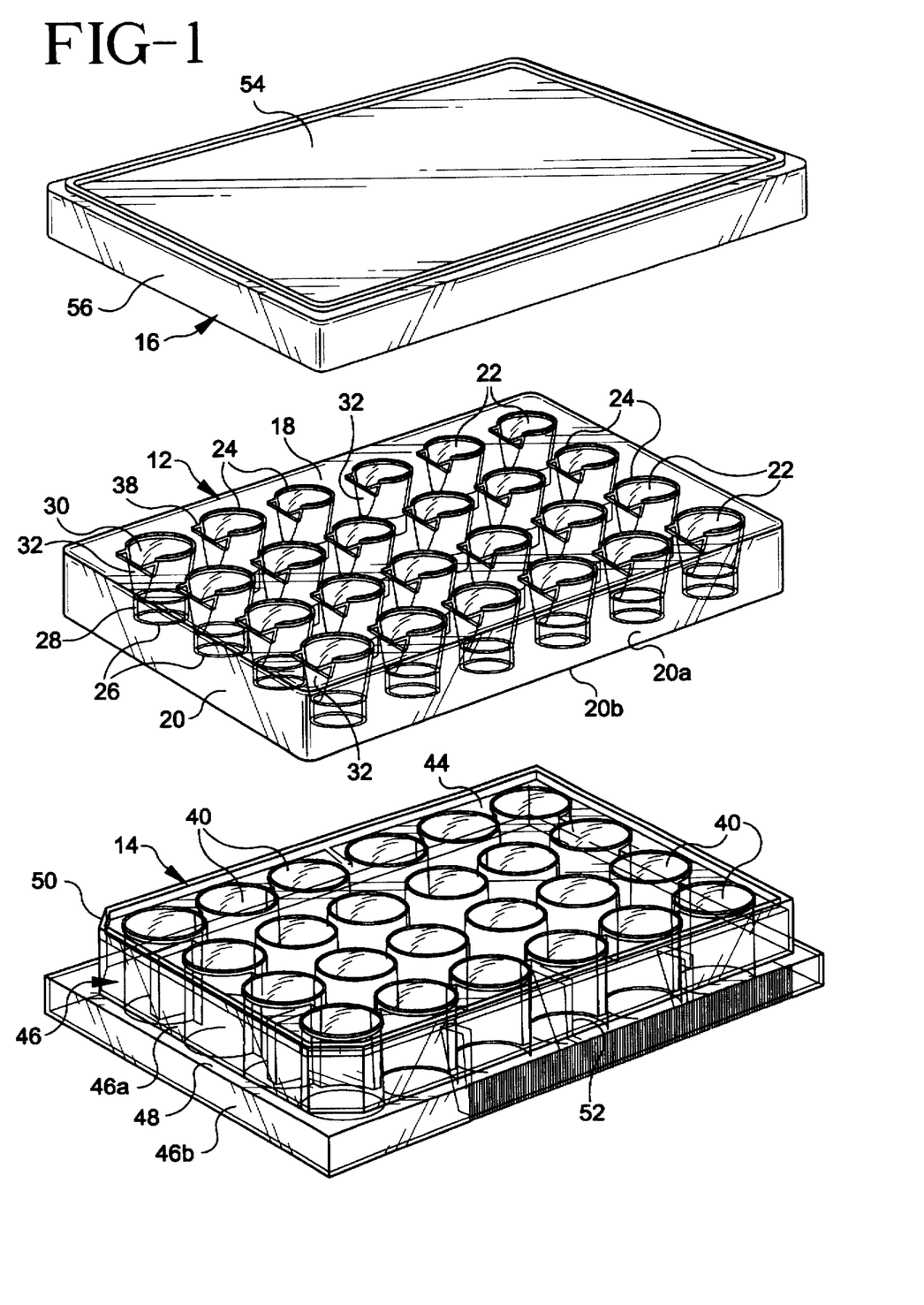
FIG. 1 is an exploded, top perspective view of a culture dish assembly in accordance with the invention.
Figure 9:
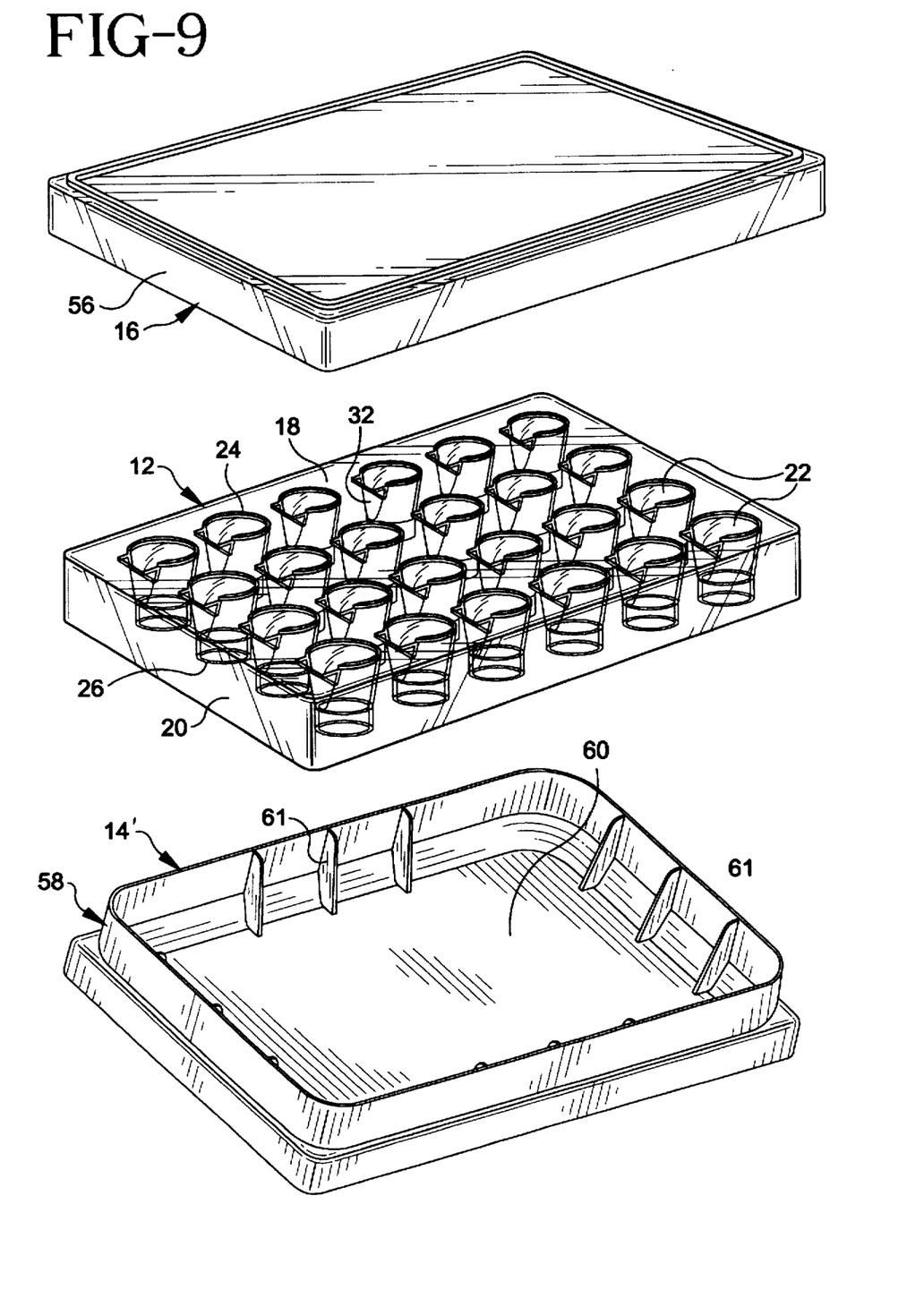
FIG. 9 is a top perspective view of a culture dish assembly according to an alternative embodiment of the invention.

A culture dish assembly 10 is provided which includes a well insert 12 and a well plate 14 capable of receiving the insert. FIG. 1 provides an exploded, perspective view of such an assembly in addition to a lid 16 which is mountable to the well insert 12. An alternative embodiment is shown in FIG. 9, where the well plate 14' defines one large well or trough as opposed to a plurality of wells. This type of well plate may be referred to as a feeder tray.

The insert 12 includes a substantially planar top wall 18 and a peripheral flange 20 extending downwardly from the top wall. The top wall conforms in configuration to the upper surface of the well plate, which is rectangular in the preferred embodiment of the invention. The flange 20 forms a slightly oblique angle with the top wall 18 to facilitate application of the insert to the well plate. The flange 20 has an inside surface 20a and a lower edge 20b; in a preferred embodiment the lower edge 20b is slightly chamfered or beveled toward the inside surface 20a of flange 20.

A plurality of enclosures 22 are coupled to the top wall 18 and extend downwardly therefrom. The enclosures are preferably arranged in rows as shown in the figures. While the insert shown in the drawings includes twenty-four enclosures, other inserts are contemplated including six, twelve, forty-eight and ninety-six enclosures, which are among the standard numbers of such enclosures used in the trade. The spacing among enclosures also preferably conforms to trade standards. In the preferred embodiment of the invention, the enclosures are formed integrally with the top wall from a transparent material such as polystyrene. In any event, they are preferably coupled permanently to the top wall, though there may be instances in which it would be desirable for the enclosures to be removable from the top wall.

Each enclosure includes an upper end 24 defining an upper opening and a lower end 26 defining a bottom opening. A side wall 28, which is preferably generally frustoconical, connects the upper and lower ends. A radial opening 30 extends through the side wall and a portion of the upper end of each enclosure. The side wall includes a substantially vertical flat portion 32 adjoining the radial opening and extending towards the lower end of the enclosure. As discussed below, this substantially vertical portion of the side wall 28 of the enclosure results in a relatively large space between one side of the enclosure and a well wall which opposes this side wall portion.

Figure 3:
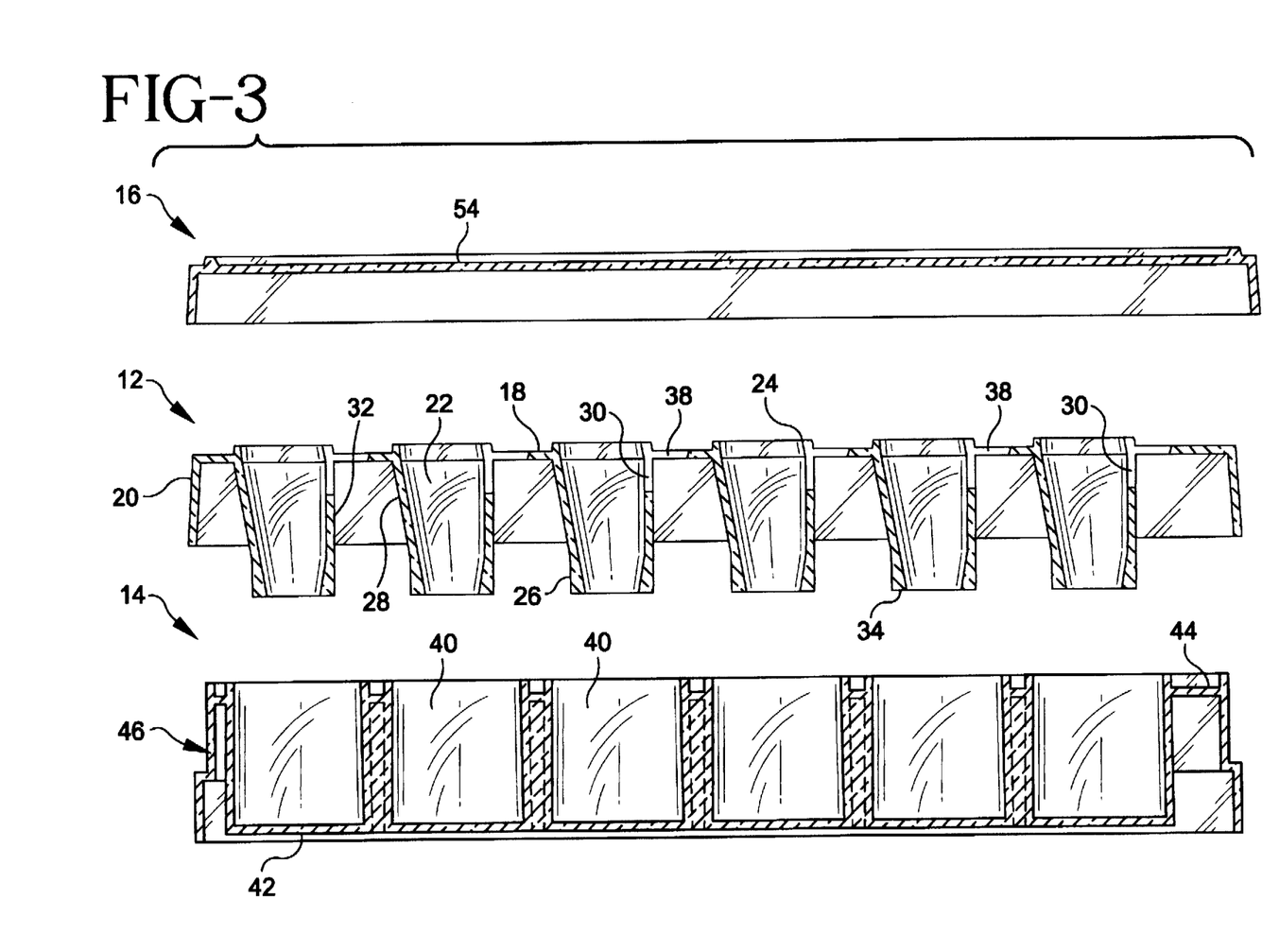
FIG. 3 is an exploded sectional view of the culture dish assembly.
Figure 4:
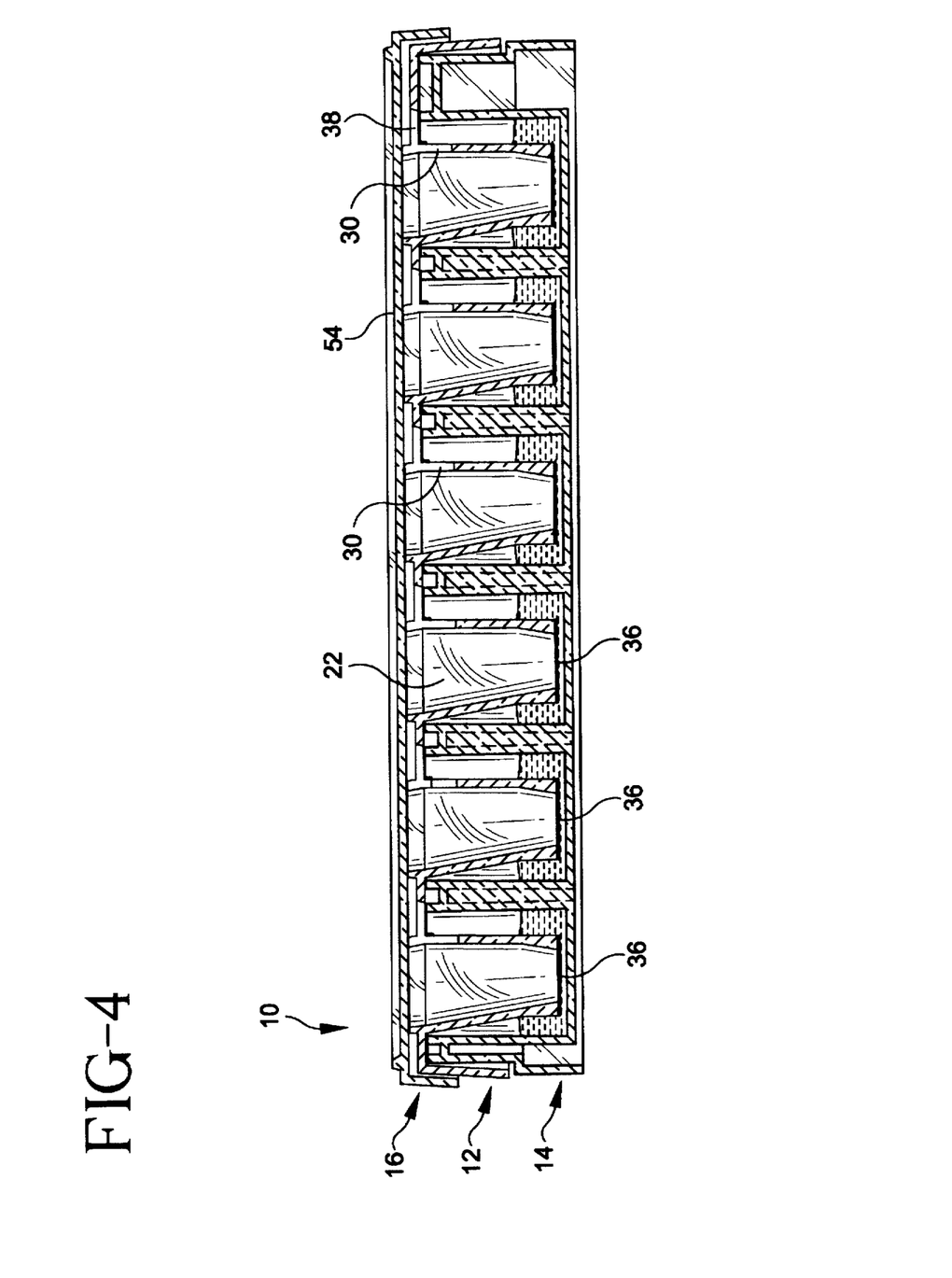
FIG. 4 is a sectional, elevation view of the culture dish assembly.
Figure 5:
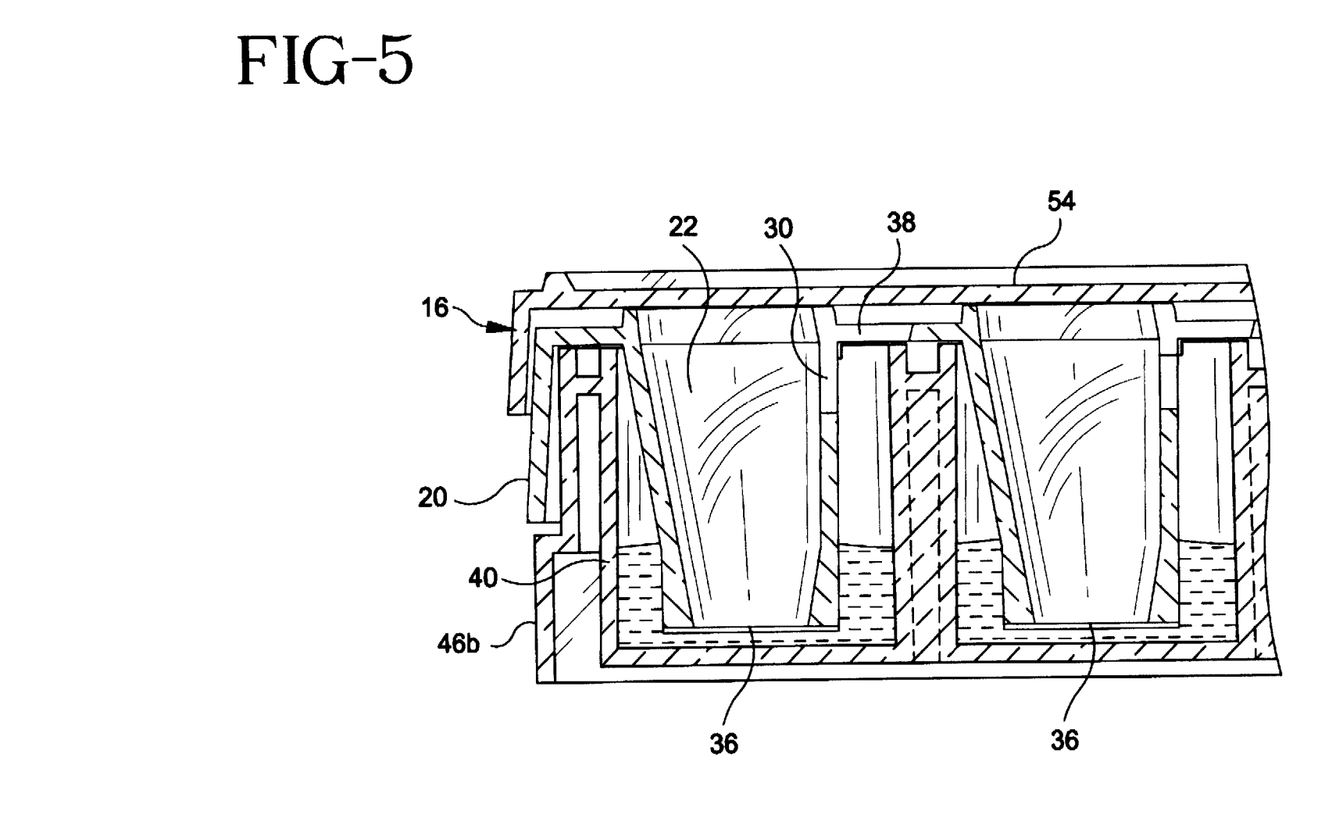
FIG. 5 is an enlarged, sectional view of an end portion of the culture dish assembly.
Figure 6:
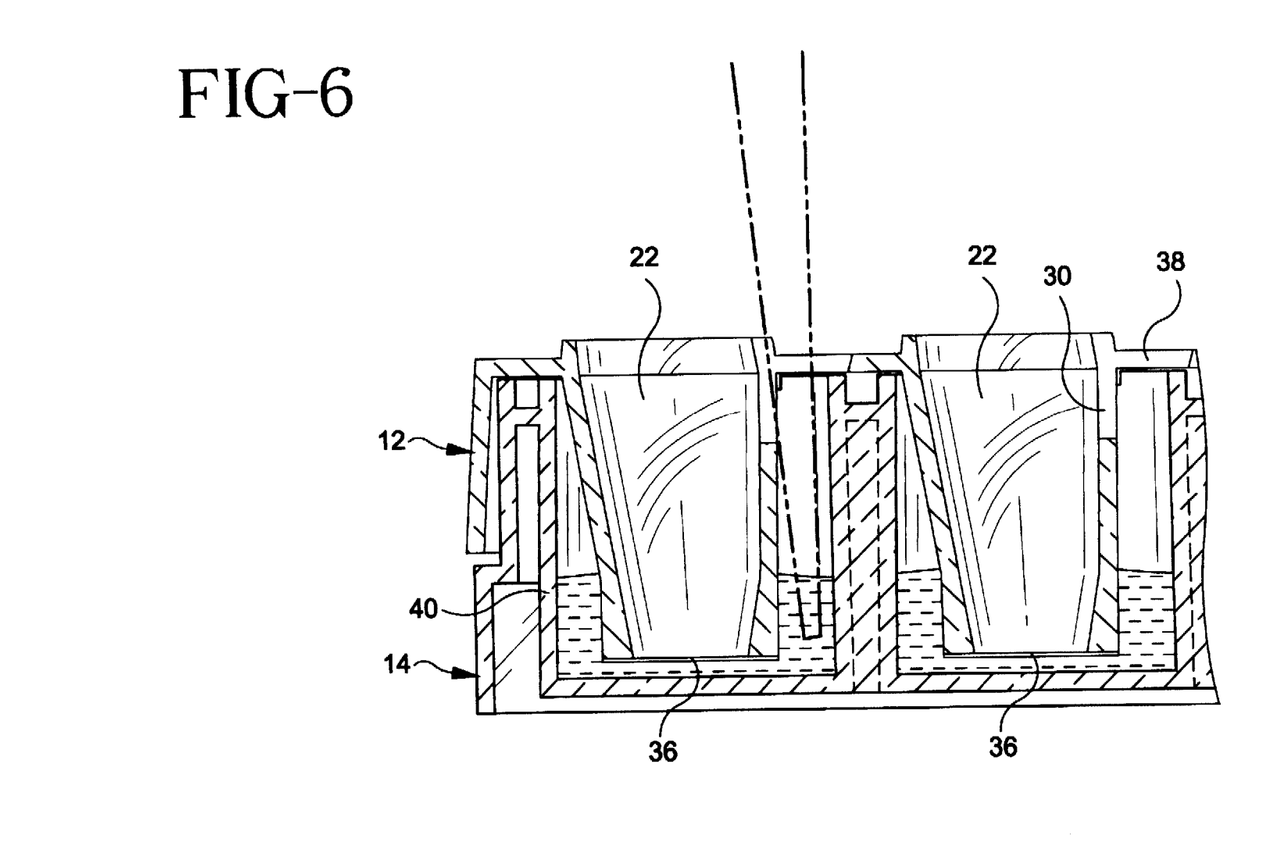
FIG. 6 is an enlarged, sectional view of an end portion of the culture dish assembly showing the insertion of a pipette into a selected portion thereof.
Figure 7:
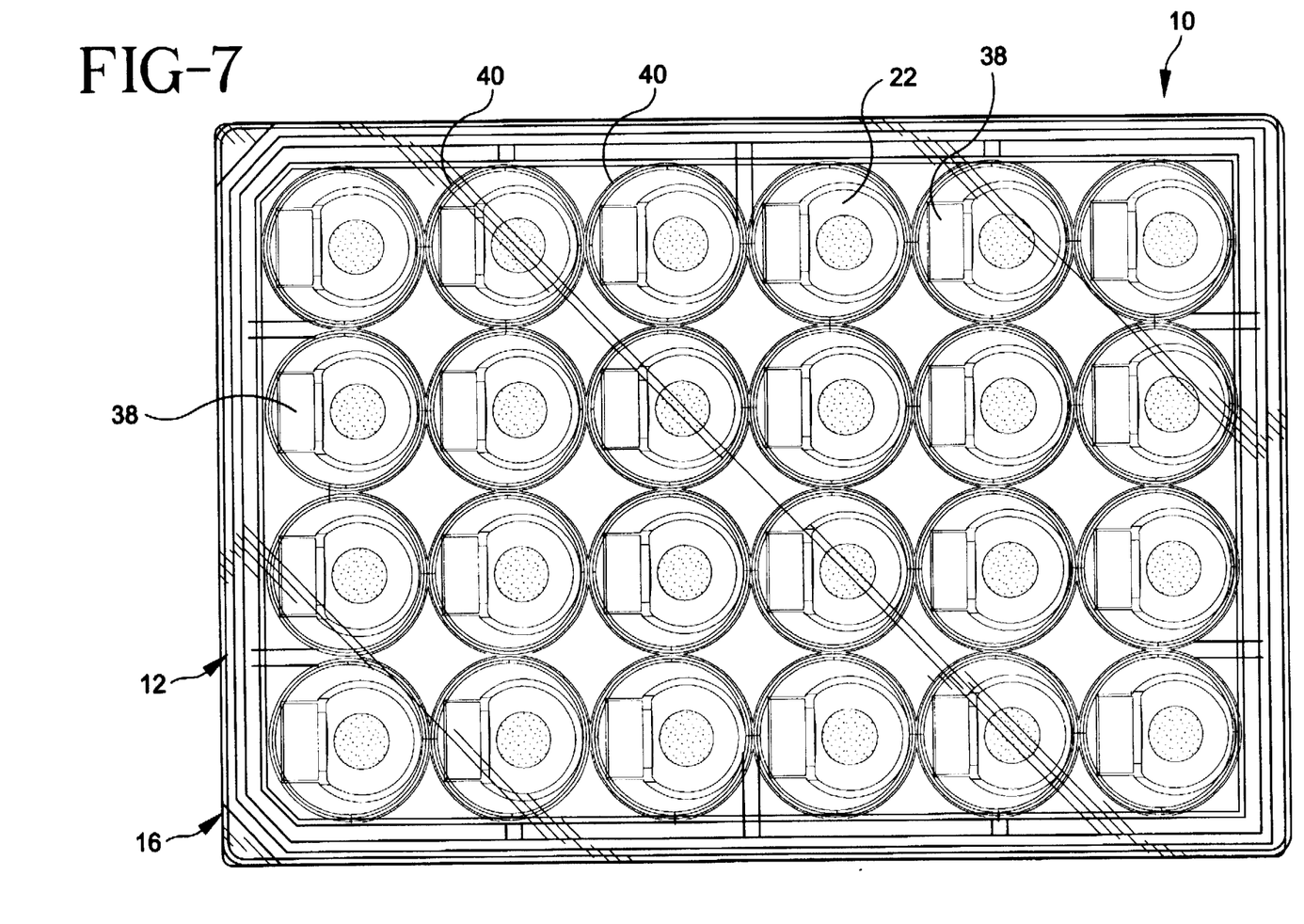
FIG. 7 is a top plan view of the culture dish assembly.
Figure 8:
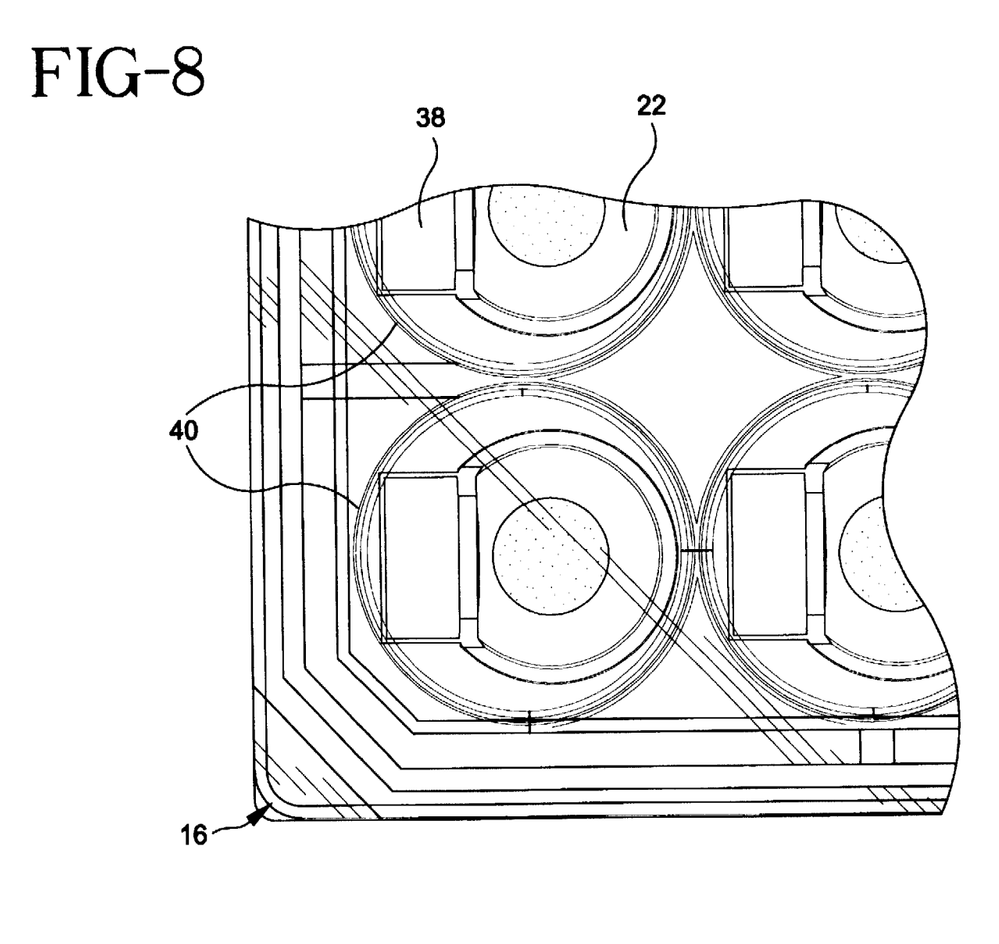
FIG. 8 is an enlarged, top plan view of a corner portion thereof.

The lower end of each enclosure includes an annular end face 34, as shown in FIG. 3. A semipermeable, microporous membrane 36 is affixed to this end face, as shown in FIGS. 4–6. The composition and pore size of the membrane is largely determined by the intended use of the culture dish assembly, as many membranes are known and available to the trade. Such membranes may be hydrophobic or hydrophilic, and made from such materials as perforated inert film, hydrated gel, cellulose, track-etched PET, polyacrylonitrile or polytetrafluoroethylene. Other microporous membranes could be employed at the discretion of the end user. The membrane is applied to the end face 34 using known techniques such as heat sealing or adhesive bonding. The assembly 10 may be provided to end users without membranes to allow them to affix the particular membranes that they prefer.

As shown in FIGS. 3–6, the upper ends of the enclosures extend above the upper surface of the top wall of the insert 12. The upper end faces of the enclosures are substantially C-shaped due to the radial openings therein. A plurality of wall openings 38 extend through the top wall of the insert and respectively adjoin the radial openings 30 in the enclosures. The wall openings are preferably, though not necessarily rectangular. The wall openings and radial openings define a plurality of pipette openings which allow pipette access to selected portions of the well plate, as shown in FIG. 6.

The well plate 14 is conventional in design, and is preferably made from a transparent material such as polystyrene. It includes a plurality of wells 40 arranged in rows. The numbers of wells and enclosures in the well plate and insert are not critical, but are preferably equal in number. Each of the wells is preferably cylindrical. The wells are joined to each other by rib portions extending between the side walls thereof In addition, each of the wells shares a common bottom wall 42. The well plate 14 further includes a top wall 44 which is integral with the outer surfaces of the wells located along the peripheral portions thereof. A peripheral wall 46 extends downwardly from the top wall 44. It includes an upper portion 46A and a lower portion 46B, with a shoulder or step 48 separating these portions. The upper wall portion includes a pair of chamfered corners 50. Ribs 52 connect selected portions of the wells to the peripheral wall 46. The well plate 14 and insert 12 are constructed such that the insert can only be mounted to the well plate in one direction.

The lid 16 is conventional in construction, and includes a rectangular top wall 54 and a downwardly depending peripheral flange 56 extending at a slightly oblique angle with respect thereto. It is made from a transparent material such as polystyrene. The bottom surface of the top wall of the lid engages the upper ends 24 of the enclosures 22 when the lid is applied to the insert 12.

As shown in FIG. 9, the insert 12 may be mounted to a plate 14' defining one large trough or well so that the membranes 36 can be immersed in a common bath. The plate 14' includes a stepped peripheral wall 58 and a bottom wall 60. Ribs 61 connect the bottom and peripheral walls, thereby adding strength to the plate. The number of ribs 61 may be increased to add rigidity, as known to the art. In addition to providing added rigidity, the presence of a plurality of ribs 61 provides a baffle effect within the plate 14', by reducing the movement or turbulence caused within the media of the media as a result of the plate being moved. The upper surface of the peripheral wall is engageable with the bottom surface of the top wall 18 of the insert 12.

The assembly 10 may be provided to end users as shown in FIGS. 1–3 and 9. Alternatively, he assemblies may be manufactured and sold with membranes 36 already secured to the enclosures 22. Once the membranes are secured, the insert 12 is ready for use. The insert 12 is mounted to the well plate 14 such that the bottom surface of the top wall 18 engages the rim portions of the wells 40, and point contacts are made between the side wall 28 of each enclosure and the inner edge of the upper rim of each well 40. The membranes are suspended above the bottom surfaces of the wells, as shown in FIGS. 4–5, when the insert is properly mounted. The membranes should be one to three millimeters above the upper surface of the bottom wall 42. The peripheral flange 20 of the insert 12 overlies the upper portion 46A of the flange of the well plate, and is suspended above the step 48. Each enclosure 22 is radially offset with respect to the well in which it is positioned, producing relatively large spaces between the enclosures and the opposing portions of the wells. The radial openings adjoin these relatively large spaces. Moreover, these spaces are further enlarged by the irregular configurations of the enclosures, particularly the flat surfaces 32 which border upon them. The wall openings 38 in the top wall 18 of the insert are positioned directly above the spaces between the enclosures and the wells. As shown in FIG. 6, the offset positions of the wells combined with the flat surfaces of the enclosures and the adjoining radial openings and wall openings greatly facilitate access to the bottom portions of the wells 40 with a pipette (shown in broken lines). The lid 16 is mounted to the insert 12 and engages the C-shaped rims of the enclosures. Evaporation from the wells and exposure to airborne contaminants such as dust or bacteria are accordingly minimized. As shown in FIG. 4, the peripheral flange 56 of the lid extends only partially over the peripheral flange 20 of the insert 12. This feature is important in that it allows the lid and insert to be removed from and reapplied to the well plate as a unit, thereby reducing the possibility of contamination. This may be accomplished manually or robotically.

Figure 2:
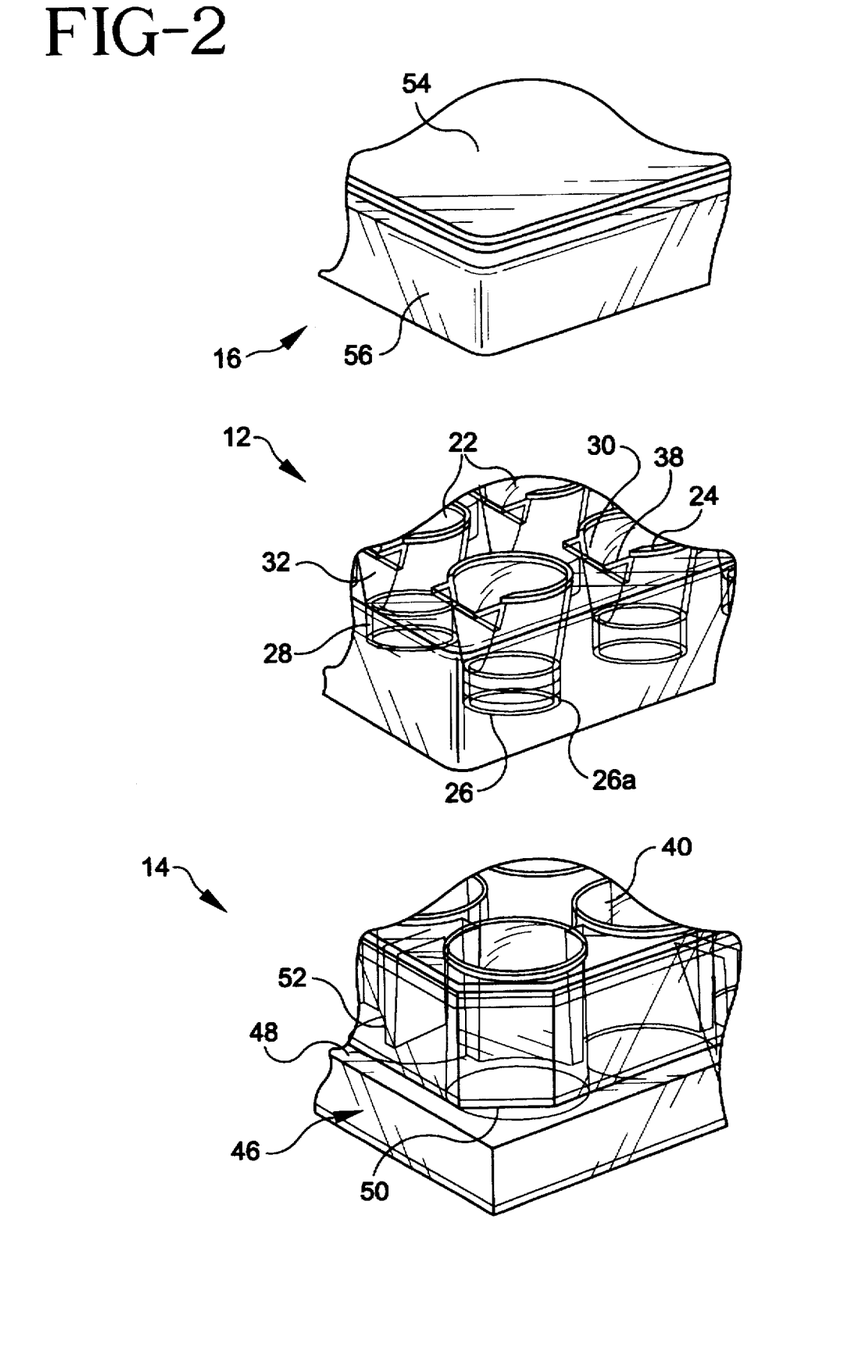
FIG. 2 is an enlarged, top perspective view of a corner portion of the culture dish assembly.

Since, each enclosure 22 of insert 12 is radially offset with respect to the well within well plate 14 in which it is positioned some wicking occurs between the side wall 28 of enclosure 22 and the well 40 of the well plate 14, therefore it is preferred that the outside of sidewall 28 in the proximity of the lower end 26 have a plurality of concentric rings 26a on side wall 28; these concentric rings 26a inhibit wicking of the media between the sidewall 28 of insert 12 and the well 40 of the well plate 14, see FIG. 2.

For those procedures or tests which require immersion of the membranes in a common bath, the assembly of FIG. 9 may be employed. When mounted to the well plate 14' shown in this figure, the membranes secured to the enclosures of the insert 12 will be suspended above the bottom wall 60 of the well plate. In both embodiments of the invention, experiments can be observed without removing the lid or any other components as they are all substantially transparent.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A culture dish assembly comprising:

a well plate defining at least one well;

an insert including a top wall and a plurality of enclosures coupled to said top wall, each of said enclosures including an upper end defining an upper opening, a lower end defining a bottom opening, a side wall connecting said upper and lower ends, a semipermeable membrane mounted to said lower end and covering said bottom opening, a plurality of wall openings in said top wall, each of said wall openings adjoining one of said enclosures, each of said enclosures including a radial opening extending through said side wall and said upper end, each of said side walls including a substantially vertical portion adjoining said radial opening and extending towards said lower end, said radial openings each adjoining one of said wall openings and defining therewith a plurality of pipette openings, said insert being mountable to said well plate such that at least one of said enclosures is positioned within said well.

2. A culture dish assembly as described in claim 1, wherein said well plate includes a plurality of substantially cylindrical wells, said insert being mountable to said well plate such that each of said enclosures is positioned within one of said wells and radially offset with respect to said well, and said wall openings are in registration with said wells.

3. A culture dish assembly as described in claim 2, wherein said side walls of said enclosures are generally frustoconical, said vertical portions of said side walls including substantially flat exterior surfaces.

4. A culture dish assembly as described in claim 3, wherein said top wall adjoins said upper ends of each of said enclosures.

5. A culture dish assembly as described in claim 4, wherein said upper ends of said enclosures extend slightly above said top wall.

6. A culture dish assembly as described in claim 5, including a lid mountable to said insert, said lid being engageable with said upper ends of said enclosures.

7. A culture dish assembly as described in claim 1 including a lid mountable to said insert, said insert including a peripheral flange extending downwardly from said top wall, said lid including a peripheral flange of lesser height than said peripheral flange of said insert, said peripheral flange of said lid being positionable about an upper portion of said peripheral flange of said insert.

8. A culture dish assembly as described in claim 7, wherein said well plate includes a peripheral wall including a lower portion, an upper portion, and a step formed between said upper and lower portions, said insert being mountable to said well plate such that said peripheral flange of said insert is suspended above said step.

9. A culture dish assembly as described in claim 1, wherein each of said side walls of said enclosures is generally frustoconical and each of said substantially vertical portions includes a substantially flat exterior surface.

10. A culture dish assembly as described in claim 1, wherein said well plate includes a plurality of rows of substantially cylindrical wells, said insert being mountable to said well plate such that each of said enclosures is positioned within one of said wells and radially offset with respect to said well, and said wall openings are in registration with said wells.

11. A culture dish assembly as described in claim 2, wherein each of said wells includes an upper rim, said side walls of said enclosures respectively bearing against inner portions of said upper rims of said wells.

12. An insert for a culture dish assembly, comprising:

a top wall including at least one row of wall openings, and a plurality of enclosures coupled to said top wall and respectively adjoining said wall openings, each of said enclosures including an upper end defining an upper opening, a lower end defining a bottom opening, a side wall connecting said upper and lower ends, a radial opening extending through said side wall and a portion of said upper end, each of said radial openings adjoining one of said wall openings, each of said side walls of said enclosures including a substantially vertical portion adjoining said radial opening and extending towards said lower end.

13. An insert as described in claim 12, wherein each of said side walls is generally frustoconical.

14. An insert as described in claim 13, wherein each of said substantially vertical portions of said side walls of said enclosures includes a substantially flat exterior surface.

15. An insert as described in claim 14, wherein each of said upper ends of said enclosures includes a generally C-shaped rim extending above said top wall.

16. An insert as described in claim 12 including a peripheral flange extending downwardly from said top wall.

17. An insert as described in claim 13, wherein each of said enclosures includes a microporous membrane secured to said lower end thereof and covering said bottom opening.

18. An insert as described in claim 12, wherein each of said side walls is generally frustoconical, and said enclosures are arranged in a row parallel to said row of wall openings.

19. A culture dish assembly comprising:

a well plate defining a plurality of wells;

an insert including a top wall, a peripheral flange extending downwardly from said top wall, said peripheral flange including an upper portion and a lower portion, and a plurality of enclosures coupled to said top wall, each of said enclosures including an upper end defining an upper opening, a lower end defining a bottom opening, a side wall connecting said upper and lower ends, a semi-permeable membrane mounted to said lower end and covering said bottom opening, a plurality of wall openings in said top wall, each of said wall openings adjoining one of said enclosures, each of said enclosures including a radial opening extending through said side wall and said upper end, each of said side walls including a substantially vertical portion adjoining said radial opening and extending towards said lower end, said radial openings each adjoining one of said wall openings and defining therewith a plurality of pipette openings, said insert being mountable to said well plate such that said enclosures are respectively positioned within and radially offset with respect to said wells, and a lid including a top wall and a downwardly depending peripheral flange, said lid being mountable to said insert such that said top wall of said lid engages said upper ends of said enclosures, said peripheral flange of said lid overlies said upper portion of said peripheral flange of said insert and said lower portion of said peripheral flange of said insert is accessible beneath said peripheral flange of said lid, thereby allowing said insert and lid to be removed from or applied to said well plate as a unit.

20. A culture dish assembly as described in claim 19, wherein each of said wells is substantially cylindrical, each of said enclosures is substantially frustoconical, each of said side walls of said enclosures includes a substantially flat, vertical portion adjoining said radial opening and extending towards said lower end.

* * * * *